United States Patent [19]

Shelton

[11] Patent Number: 5,387,228
[45] Date of Patent: Feb. 7, 1995

[54] CARDIAC PACEMAKER WITH PROGRAMMABLE OUTPUT PULSE AMPLITUDE AND METHOD

[75] Inventor: Michael B. Shelton, Minneapolis, Minn.

[73] Assignee: Medtronic, Inc., Minneapolis, Minn.

[21] Appl. No.: 81,911

[22] Filed: Jun. 22, 1993

[51] Int. Cl.[6] .............................................. A61N 1/36
[52] U.S. Cl. ..................................................... 607/11
[58] Field of Search ................................... 607/11, 12

[56] References Cited

U.S. PATENT DOCUMENTS

| | | |
|---|---|---|
| 3,057,356 | 10/1962 | Greatbach . |
| 3,478,746 | 11/1969 | Greatbach . |
| 3,557,796 | 1/1971 | Keller . |
| 3,631,860 | 1/1972 | Lopin . |
| 3,805,796 | 4/1974 | Terry, Jr. et al. . |
| 3,833,005 | 9/1974 | Wingrove . |
| 3,857,399 | 12/1974 | Zacouto . |
| 3,865,119 | 2/1975 | Svensson et al. . |
| 3,870,050 | 3/1975 | Greatbach . |
| 4,038,991 | 8/1977 | Walters . |
| 4,043,347 | 8/1977 | Renirie . |
| 4,049,003 | 9/1977 | Walters et al. . |
| 4,049,004 | 9/1977 | Walters . |
| 4,066,086 | 1/1978 | Alferness et al. . |
| 4,231,027 | 10/1980 | Mann et al. . |
| 4,250,883 | 2/1981 | Thompson . |
| 4,259,639 | 3/1981 | Renirie . |
| 4,324,251 | 4/1982 | Mann . |
| 4,340,062 | 7/1982 | Thompson et al. . |
| 4,590,941 | 5/1986 | Sawson et al. ............... 607/11 |
| 5,137,020 | 8/1992 | Wayne et al. . |
| 5,052,388 | 10/1991 | Sivula et al. . |

OTHER PUBLICATIONS

"Digital Timing Unit for Programming Biological Stimulators", American Journal of Medical Electronics, First Quarter, 1977, pp. 29–34.

Primary Examiner—William E. Kamm
Assistant Examiner—Scott M. Getzon
Attorney, Agent, or Firm—Harold R. Patton

[57] ABSTRACT

An implantable cardiac pacemaker having programmable stimulating pulse amplitudes selectable by means of an external programming unit. The pacemaker includes charge pump circuitry for developing a stimulating pulse voltage on an output capacitor. The output capacitor is charged to a selected level identified by a multiple-bit amplitude value communicated to the implanted device from the external programmer. The pacemaker is also provided with circuitry for monitoring the depletion level of its battery and for generating an indicator signal when the battery has depleted beyond a predetermined level. Associated with the charge pump circuitry is a selectively activated comparator circuit for controlling the charging of the output capacitor. Prior to generation of the indicator signal, the charge pump circuitry remains deactivated for some programmed output amplitudes, the level of output capacitor charging being proportional to the battery voltage. After issuance of the indicator signal, the comparator circuit is activated to control the charging of the output capacitor. When the comparator circuit is activated for charging the capacitor, the resulting voltage established on the capacitor is proportional to a predetermined constant reference voltage. Longevity of the device is optimized by not activating the comparator circuit during early stages of battery depletion when the battery's output voltage is relatively stable.

6 Claims, 6 Drawing Sheets

| BIT 7 (MSB) | | | | | | | BIT 0 (LSB) |
|---|---|---|---|---|---|---|---|
| (not used) | AUNB | ACPD | AREG | AAS3 | AAS2 | AAS1 | AAS0 |

| BIT 7 (MSB) | | | | | | | BIT 0 (LSB) |
|---|---|---|---|---|---|---|---|
| SAVB | VUNB | VCPD | VREG | VAS3 | VAS2 | VAS1 | VAS0 |

CARDIAC PACEMAKER WITH PROGRAMMABLE OUTPUT PULSE AMPLITUDE AND METHOD

FIELD OF THE INVENTION

This invention relates to the field of implantable medical devices, and more particularly relates to implantable medical devices capable of generating output stimulating pulses at selectable energy levels.

BACKGROUND OF THE INVENTION

Since the introduction of the first implantable pacemakers in the early 1960s, there have been considerable advancements both in the field of electronics and in the field of medicine, such that there is presently a wide assortment of commercially-available implantable medical devices. The class of implantable medical devices now includes not only pacemakers, but also implantable cardioverters, defibrillators, neural stimulators, and the like. Today's state-of-the-art implantable medical devices are vastly more sophisticated and complex than early pacemakers, and are capable of performing significantly more complex functions. The therapeutic benefits of implantable medical devices have been well proven.

An early pacemaker was disclosed in U.S. Pat. No. 3,057,356 issue to Greatbatch in 1962 and entitled "Medical Cardiac Pacemaker". The Greatbatch pacemaker included a relaxation oscillator for controlling the pacemaker to generate electrical cardiac stimulating pulses. Thus, the pacemaker operated asynchronously to provide fixed-rate cardiac stimulation not automatically changed in accordance with the patient's needs. The Greatbatch pacemaker proved to be effective in alleviating the symptoms of complete heart block. As an asynchronous device, however, the Greatbatch pacemaker had the possible disadvantage of operating to compete with the natural, physiological functioning of the heart during episodes of normal sinus condition.

Since 1962, implantable pulse-generating medical devices have been continuously evolving. For example, in order to overcome the possible disadvantages with asynchronous pacemakers, implantable pacemakers of the synchronous or demand type were developed wherein stimulating pulses are delivered only when required, and are not delivered when the heart functions with a normal sinus rhythm. An early demand-type pacemaker is disclosed, for example, in U.S. Pat. No. 3,478,746 entitled "Cardiac Implantable Demand Pacemaker". The demand pacemaker solves the problem arising with asynchronous pacemakers by inhibiting delivery of stimulating pulses in the presence of detected ventricular activity, and by delivering stimulating pulses only in the absence of natural cardiac activity.

Another improvement which occurred since the first implantable cardiac pacemaker is the ability to reprogram certain operational parameters of the pacemaker after it has been implanted. For example, in U.S. Pat. No. 3,805,796 issued to Terry, Jr. et al. in 1974 and entitled "Implantable Cardiac Pacemaker Having Adjustable Operating Parameters". The Terry, Jr. device included circuitry to allow the rate of the pacemaker to be non-invasively changed after the device was implanted. The stimulation rate was varied according to the number of times that a magnetically actuated reed switch was closed. The device operated to count the number of times the reed switch was closed and storing that count in a binary counter. Each state of the counter was connected to either engage or bypass one resistor in a serially-connected resistor chain, where the resistor chain formed part of the RC time constant controlling pacemaker rate.

The concept of the Terry, Jr. patent has also been improved upon, as exemplified in U.S. Pat. No. 4,066,086 to Adams et al. entitled "Programmable Body Stimulator" The Adams et al. patent discloses a pacemaker that responds to the application of radio frequency (RF) bursts while a magnetic filed held in close proximity to a reed switch in the device holds the reed switch closed. In the adams et al. circuit, only the rate is programmable in response to the number of RF bursts applied. The use of RF signals to program cardiac pacemakers was earlier disclosed in U.S. Pat. No. 3,833,005 issued to Wingrove in 1974 and entitled "Compared Count Digitally Controlled Pacemaker". The Wingrove device was capable of having both pacing rate and pacing pulse width programmed.

Perhaps the most significant advance in implantable device technology, however, was the incorporation of digital circuitry in implantable devices. Implantable device technology initially lagged behind conventional state-of-the-art electronic technology in its utilization of digital circuits. A primary reason for the delay in was that early digital circuits consumed unacceptably large amounts of energy to be used in battery-powered implantable devices impractical. Of course, conservation of battery power in implantable devices has always been a major concern in pacemaker design. Thus, although there were suggestions in the art to utilized digital techniques in cardiac pacemakers even as early as 1966 (see, e.g., Walsh et al., "Digital Timing Unit for Programming Biological Stimulators", *American Journal of Medical Electronics*, First Quarter, 1977, pp. 29–34), the first patent suggesting digital techniques in the context of cardiac pacemakers was U.S. Pat. No. 3,557,796 issued to Keller, Jr., et al. in 1971 and entitled "Digital Counter Driven Pacer".

The Keller, Jr. pacemaker included an oscillator driving a binary counter. When the counter reached a certain value, a signal was provided which caused a cardiac stimulating pulse to be provided. At the same time, the counter was reset and began counting oscillator pulses. The Keller, Jr. pacemaker also incorporated a demand feature, wherein the counter was reset upon detection of a natural heartbeat, as well as a refractory feature, wherein output pulses were inhibited for a certain time after the provision of a cardiac stimulating pulse or natural beat.

Improvements in digital technology and in battery technology have been such that the use of digital circuitry in implantable devices has, over the years, become increasingly feasible and increasingly common. Patents disclosing digital techniques useful in cardiac pacemakers include U.S. Pat. No. 3,631,860 to Lopin entitled "Variable Rate Pacemaker"; U.S. Pat. No. 3,857,399 to Zacouto entitled "Heart Pacer"; U.S. Pat. No. 3,865,119 to Svensson et al. entitled "Heartbeat Accentuated with Controlled Pulse Amplitude"; U.S. Pat. No. 3,870,050 to Greatbatch entitled "Demand Pacer"; U.S. Pat. No. 4,038,991 to Walters entitled "Cardiac Pacer with Rate Limiting Means"; U.S. Pat. No. 4,043,347 to Renirie entitled "Multiple-Function Demand Pacer with Low Current Drain"; U.S. Pat. No. 4,049,003 to Walters et al. entitled "Digital Cardiac Pacer"; and U.S. Pat. No. 4,049,004 to Walters entitled "Implantable Digital Cardiac Pacer Having Externally Selectable Operating Parameters and One-Shot Digital Pulse Generator for Use Therein".

Pacemakers incorporating digital circuitry are also disclosed in U.S. Pat. No. 4,250,883 issued to David L. Thompson and entitled "Digital Cardiac Pacemaker"; and in U.S. Pat. No. 5,052,388 to Sivula et al. entitled "Method and Apparatus for Implementing Activity Sensing in a Pulse Generator". The Thompson '883 and Sivula et al. '388 patents are hereby incorporated by reference herein in their respective entireties.

The accuracy and reliability of digital circuits are factors that have encouraged their use in implantable devices. Their ability to be programmed and reprogrammed to alter one or more operating parameters further enhances their utility. For example, the pacemaker disclosed in the above-referenced Sivula et al. patent respond to radio frequency signals from a microprocessor-based external programming unit to alter numerous operating parameters, including pulse rate, pulse width and/or pulse amplitude, pacing mode, sensing mode and sensitivity, activity/rate response settings, refractory periods, AV-delay settings, and others. In U.S. Pat. No. 4,340,062 to Thompson et al. entitled "Body Stimulator Having Selectable Stimulation Energy Levels", there is disclosed a pacemaker in which the amplitude, duration, and repetition rate of cardiac stimulating pulses is externally controllable. The Thompson '062 patent is hereby incorporated by reference herein in its entirety.

Since digital technology has made it possible to provide numerous non-invasively programmable parameters in implantable devices, it is now relatively common for pacemakers to provide for a plurality of different stimulating pulse amplitude settings. One reason for the desirability of having programmable pulse amplitude in a pacemaker is that battery longevity can be maximized through selection of a pacing pulse amplitude appropriate for a given patient's pacing threshold. That is, for a patient with a relatively low pacing threshold, the pacing amplitude can be set to a correspondingly lower level than for a patient with a higher pacing threshold, thereby minimizing power consumption while at the same time ensuring that the pacing pulses will be sufficient to capture the patient's heart.

One difficulty in implementing programmable pulse amplitude in a pacemaker is ensuring that pacing pulses will be delivered at the selected pacing amplitude throughout the life of the pacemaker, even though the battery voltage will not remain at the same level at all battery depletion levels. Typically, implantable pulse generator utilize output capacitors to store the energy for an output pulse. Charging circuitry is provided to couple the output capacitors to the battery prior to delivery of a pulse. The charge accumulated on the output capacitors can be controlled, for example, by controlling the amount of time that the output capacitors are coupled to the battery voltage. However, such an arrangement assumes that the battery voltage remains the same throughout its life, the output capacitors always charging to the same voltage for a given charging interval. This, of course, is not a valid assumption.

To overcome the problem of declining battery voltage with battery discharge, a pacemaker may be provided with circuitry for controlling the process of charging of the output capacitors. For example, when an output capacitor is to be charged to a chosen voltage, the output capacitors may be coupled to a battery and to a comparator circuit. The charging circuit can then operate to keep the output capacitors coupled to the battery until the comparator circuit indicates that the desired voltage level has been reached, at which time the charging of the capacitors is discontinued. This arrangement does not assume a constant battery voltage for all depths of battery discharge, but has the drawback of increasing the complexity of the charging circuitry. Also, the regulation circuitry itself consumes power and thus increases the device's overall current consumption and reduces its projected longevity.

Lithium-iodine batteries are among the most commonly used power sources for modern implantable devices, and much has come to be known about their depletion characteristics. In particular, it is well known in the art that the output voltage from lithium-iodine batteries is relatively linear during early stages of depletion, but drops off rather sharply before end-of-life (EOL). This is due in part to the internal resistance of lithium-iodine batteries, which is relatively linear as a function of energy depletion until near EOL, at which time the resistance curve exhibits a "knee" where internal resistance begins to rise rapidly.

In typical lithium-iodine batteries, the cell cathode consists of molecular iodine weakly bonded to polyvinyl pyridine (P2VP). The initial cathode composition of lithium-iodine batteries is often expressed as the weight ratio of $I_2$ to P2VP. Typical values of this ratio range from 20:1 to 50 1. No electrolyte as such is included in the construction of the cell, but a lithium iodine (LiI) electrolyte layer forms during cell discharge, between the anode and the cathode. The LiI layer presents an effective internal resistance to Li+ions which travel through it. Since the LiI layer grows with the charge drawn from the battery, this component of the battery resistance increases linearly as a function of energy depletion. In the implantable device context, where there is typically a relatively continuous energy depletion, this component of the internal resistance increases continually over time. However, particularly for a demand type pacemaker which at any given time may or may not be called upon to deliver stimulating pulses, the increase in this component is continuous but not necessarily linear with time, due to the fact that current drain is not constant.

Another component of internal resistance in lithium-iodine cells is caused by depletion of iodine in the cathode. The cathode is essentially a charge transfer complex of iodine and P2VP, and during discharge of the cell iodine is extracted from this complex. As noted above, the weight ratio of $I_2$ to P2VP at beginning of life may range from 20:1 to 50:1. During extraction of iodine from the complex, the resistance to this process is low until the point is reached where the $I_2$-to-P2VP ratio is reduced to approximately 8:1, the ratio at which the cathode becomes a single phase and the iodine activity begins to be less than unity. At this point the resistance rises sharply. This gives rise to a non-linear internal resistance component which, for the lithium-iodine cell, is called variously the depletion resistance, depolarizer resistance, the charge-transfer complex resistance, or the pyridine resistance. By whatever names, the combination of the non-linear component with the linear component produces an overall resistance curve with a knee occurring toward EOL, the knee being caused by the reaching of the depletion of available charge carriers from the cathode.

Since it is often extremely critical for patients' wellbeing that implantable devices do not cease operating, it is common for implantable devices to monitor the level of battery depletion and to provide some indication when the depletion reaches a level at which the battery should be replaced. Pacemakers manufactured by Medtronic, Inc., for example, typically provide, for example via telemetry, an "elective replacement indictor" (ERI) when the battery depletion reaches a level such that replacement will soon be needed. Pacemakers may also provide an indication when the level battery depletion is such that the device must be replaced immediately. Other pacemakers may provide information about battery depletion levels throughout the device's life, for example, whenever the pacemaker is interrogated by an external programmer.

In the prior art, some ERI arrangements in implantable devices evaluate battery life based simply upon the terminal voltage of the battery, indicating ERI or EOL when the voltage falls below a predetermined threshold. However, due to the internal impedance characteristics of the battery, discussed above, terminal voltage can vary significantly depending upon current consumption. Thus, if relatively little current is drawn from the battery for a period of time when the battery is nearing but has not reached the ERI point, a sudden prolonged period of high demand on the battery may cause a situation in which too little time is available between ERI and total depletion of the battery. For a particular pacemaker and electrode combination in a given patient, there will be a variation in the effective load on the lithium-iodine battery, and a resulting variation in the overall current drain. Accordingly, if ERI is predicated upon sensing the voltage of the battery and detecting when it drops below a certain level, there can be very little assurance that the level chosen will correspond to the knee of the internal resistance curve.

It has been recognized in the prior art that since remaining battery life is directly related to the internal impedance of the battery itself, remaining battery life can be reliably predicted through accurate measurement of internal battery impedance. In U.S. Pat. No. 5,137,020 issued to Wayne et al. and assigned to the assignee of the present invention, there is described a battery impedance measuring arrangement wherein a current source and a reference impedance are applied to a battery which has been isolated from the remainder of the pacemaker circuitry. The Wayne et al. '020 patent is hereby incorporated by reference in its entirety into the present disclosure.

Other battery impedance measuring arrangements are proposed, for example, in U.S. Pat. Nos. 4,259,639 to Renirie, 4,231,027 to Mann et al., and 4,324,251 to Mann. These patents are also hereby incorporated by reference herein in their entirety. The theory underlying the use of internal impedance as a EOL warning indicator is that at low current drains typical of implantable medical devices, plots of resistance versus time give more warning than plots of terminal voltage over time. If voltage characteristics for different current drains are considered, the knees in the impedance curve are observed to have a fairly wide variation, meaning that the voltage at which the knee might appear is similarly subject to substantial variation as a function not only of the particular battery being used but also of the current being drawn by the pacemaker circuitry at a given time. On the other hand, plots of resistance indicate that the knee varies over a smaller range of values of internal resistance. Since the current drain may vary drastically with different electrode loads, the variation in voltage may be twice as great as the variation in internal resistance. Monitoring the internal resistance thus provides a more direct indication of the depth of discharge of the battery, whereas monitoring the output voltage gives a much less direct indication, reflecting not only the depth of discharge but also the current drain.

Provision of an ERI is not the only reason for monitoring a battery's depth of discharge. Another reason is that, as noted above, control of output pulse energy levels may also require information about the battery's output. In the prior art, it has been common to provide charge amplitude control circuitry for charging the output capacitors to a selected voltage. As previously noted, however, the charge amplitude control circuitry itself may consume battery power. In recognition of this, some pacemakers in the prior art have been designed such that when the battery reaches a particular level of depletion, the charge amplitude control circuitry is disabled, in order to minimize power consumption. This is done, for example, in the Cosmos II pacemaker manufactured and commercially available from Intermedics, Inc., Freeport, Tex. After the battery has depleted to such a level that the control circuitry is disabled, the capacitors are charged in an unregulated manner, i.e., without monitoring of the charging voltage. A worst-cause battery voltage is assumed, so that the capacitors are charged to at least some minimum level.

While this prior art arrangement eliminates current drain due to output regulation circuitry near the end of the battery's life, it has the disadvantage of reducing the pacemaker's ability to accurately control output pulse energy levels after the battery has reached a given level of depletion. In addition, such an arrangement may not be optimal in terms of device longevity. Thus, the inventor believes that there remains to be a need for improved arrangements for selecting and controlling output pulse energy levels in implanted devices.

SUMMARY OF THE INVENTION

In accordance with one feature of the present invention, therefore, a pacemaker is provided which has a plurality of programmable output pulse amplitude settings and which is capable of both regulated and unregulated output capacitor charging. In addition, the pacemaker is provided with circuitry for monitoring the depth of discharge of the battery.

In accordance with another feature of the present invention, a pacemaker is provided with output circuitry capable of producing output pulses having either "regulated" or "unregulated" amplitudes. "Regulated" amplitude output pulses have amplitudes which are proportional to a known reference voltage. That is, "regulated" amplitude output pulses have amplitudes which are known voltage values, e.g., 0.5-V to 7.5-V in 0.5-V increments. "Unregulated" amplitude output pulses have amplitudes which are proportional to the battery voltage. As such, the unregulated amplitude output pulses will have amplitudes which depend upon the current depletion level of the battery, e.g., 0.42, 0.84, 1.26. 1.68. and 2.42 times the battery voltage, which may decrease with battery depletion levels.

In accordance with still another feature of the present invention, the pacemaker takes advantage of the relatively flat output characteristic of lithium-iodine batteries during the early and middle stages of depletion, in that the pacemaker "unregulated" amplitude output pulses during these stages. Since the battery voltage is relatively constant during these stages, output pulse energy levels which are proportional to the battery output voltage will be relatively consistent, and the pulses can be generated without the need for regulation circuitry. When the battery reaches some predetermined level of depletion, however, output control circuitry is activated to ensure that output pulse energy is maintained at the selected level even though battery voltage decreases rather abruptly during the final stages of depletion.

BRIEF DESCRIPTION OF THE DRAWINGS

The foregoing and other aspects of the present invention will be best appreciated with reference to the detailed description of a specific embodiment of the invention, which follows, when read in conjunction with the accompanying drawings, wherein.

DETAILED DESCRIPTION OF A SPECIFIC EMBODIMENT OF THE INVENTION

Figure 1:
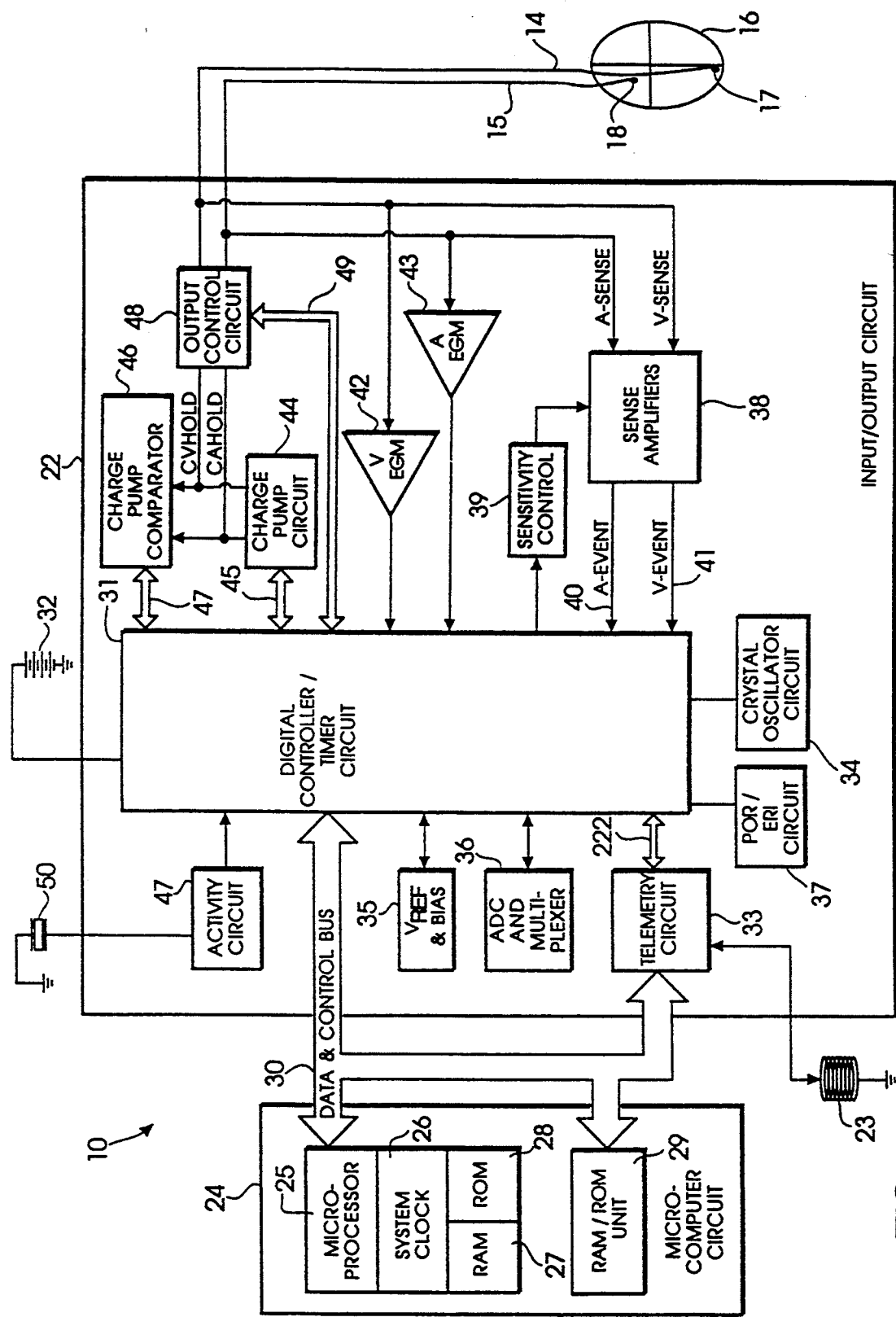
FIG. 1 is a block diagram of a cardiac pacemaker in accordance with one embodiment of the invention.

Referring to FIG. 1, there is shown a block diagram of an implantable pacemaker 10 which incorporates a telemetry subsystem in accordance with the present invention. Although the present invention will be described herein in conjunction with a pacemaker 10 having a microprocessor-based architecture, it will be understood that pacemaker 10 may be implemented in any logic based, custom integrated circuit architecture, if desired. The pacemaker shown in FIG. 1 is substantially similar to that disclosed in co-pending U.S. patent application Ser. No. 07/794,766 filed by Paul Stein and entitled "Method and Apparatus for Implementing Activity Sensing in a Pulse Generator", and in co-pending U.S. patent application Ser. No. 07/870,062 filed by Wahlstrand et al. entitled "Method and Apparatus for Rate-Responsive Cardiac Pacing". The Stein Ser. No. 07/794,766 and Wahlstrand Ser. No. 07/870,062 applications are each hereby incorporated herein by reference in their entireties.

Although a particular implementation of a pacemaker is disclosed herein, it is to be understood that the present invention may be advantageously practiced in conjunction with many different types of pacemakers, such as the pacemaker described in the above-referenced Sivula et al. patent, for example, as well as other types of implantable medical devices.

In FIG. 1, pacemaker 10 is shown to include an activity sensor 50, which may be, for example, a piezoelectric element bonded to the inside of the pacemaker's shield. Such a pacemaker/activity sensor configuration is the subject of the above-referenced patent to Anderson et al. Piezoelectric sensor 50 provides a sensor output which varies as a function of a measured parameter that relates to the metabolic requirements of a patient.

Pacemaker 10 of FIG. 1 is programmable by means of an external programming unit (not shown in FIG. 1). One such programmer suitable for the purposes of the present invention is the Medtronic Model 9760 programmer which is commercially available and is intended to be used with all Medtronic pacemakers. The 9760 programmer is a microprocessor-based device which provides a series of encoded signals to pacemaker 10 by means of a programming head which transmits radio-frequency (RF) encoded signals to pacemaker 10 according to the telemetry system laid out, for example, in U.S. Pat. No. 5,127,404 to Wyborny et al. entitled "Improved Telemetry Format", which is assigned to the assignee of the present invention and which is incorporated herein by reference in its entirety. It is to be understood, however, that the programming methodology disclosed in the above-referenced patent is identified herein for the purposes of illustration only, and that any programming methodology may be employed so long as the desired information can be conveyed between the pacemaker and the external programmer.

It is believed that one of skill in the art would be able to choose from any of a number of available pacemaker programmers and programming techniques to accomplish the tasks necessary for practicing the present invention. As noted above, however, the Medtronic Model 9760 programmer is presently preferred by the inventors.

In the illustrative embodiment of the present invention, parameters such as the lower rate of pacemaker 10 may be programmable, for example from 40 to 90 pulses per minute (PPM) in increments of 10 PPM, and the upper rate may be programmable, for example, between 100 and 175 PPM in 25 PPM increments. There may also be programmable rate response functions in pacemaker 10. In addition, pacemaker 10 has, in accordance with one embodiment of the present invention, a plurality of programmable output pulse energy settings. In particular, the output pulse energy level is programmable from 0 to 7.5-V in 0.5-V increments.

Pacemaker 10 is schematically shown in FIG. 1 to be electrically coupled via pacing lead 14 and 15 to a patient's heart 16. Leads 14 and 15 include one or more intracardiac electrodes, depending upon whether they are unipolar or bipolar leads. As would be appreciated by those of ordinary skill in the art, bipolar leads include separate, electrically isolated tip and ring electrodes, while unipolar leads include a single tip electrode. For the sake of illustration, electrodes designated as 17 and 18 are shown in FIG. 1, located near their distal ends of leads 14 and 15, respectively, and positioned within the right ventricular (RV) and right atrial (RA) chambers, respectively, of heart 16. It is to be understood, however, that leads 14 and 15 may be of either the unipolar or bipolar type as is well known in the art.

Electrodes 17 and 18 are coupled via suitable lead conductors through input/output terminals of an input-/output circuit 22. In the presently disclosed embodiment, activity sensor 50 is bonded to the inside of the pacemaker's outer, protective shield, in accordance with common practice in the art. As shown in FIG. 1, the output from activity sensor 50 is also coupled to input/output circuit 22.

Input/output circuit 22 contains the analog circuits for interface to the heart 16, activity sensor 50, an antenna 23, as well as circuits for the application of stimulating pulses to heart 16 to control its rate as a function thereof under control of the software-implemented algorithms in a microcomputer circuit 24.

Microcomputer circuit 24 comprises a microprocessor 25 having an internal system clock circuit 26, and on-board RAM 27 and ROM 28. Microcomputer circuit 24 further comprises a RAM/ROM unit 29. Microprocessor 25 and RAM/ROM unit 29 are each coupled by a data and control bus 30 to a digital controller/timer circuit 31 within input/output circuit 22. Microcomputer circuit 24 may be a commercially-available, general-purpose microprocessor or microcontroller, or may be a custom integrated circuit device augmented by standard RAM/ROM components.

It will be understood that each of the electrical components represented in FIG. 1 is powered by an appropriate implantable battery power source 32, in accordance with common practice in the art. In the presently disclosed embodiment of the invention, power source 32 is a lithium-iodine battery. Lithium-iodine batteries suitable for the purposes of the present invention are well-known and commercially-available from a number of manufacturers. For the sake of clarity, the coupling of battery power to the various components of pacemaker 10 has not been shown in the Figures.

An antenna 23 is connected to input/output circuit 22 for purposes of uplink/downlink telemetry through an RF telemetry circuit 33 in accordance with one embodiment of the invention, to be hereinafter described in greater detail. In the embodiment of FIG. 1, telemetry circuit 33 is coupled to digital controller/timer circuit 31. It is contemplated that telemetry circuit 33 may also be coupled directly to microcomputer circuit 24 via data and control bus 30.

A crystal oscillator circuit 34, typically a 32,768-Hz crystal-controlled oscillator, provides main timing clock signals to digital controller/timer circuit 31. A $V_{REF}$ and Bias circuit 35 generates stable voltage reference and bias currents for the analog circuits of input-/output circuit 22. An analog-to-digital converter (ADC) and multiplexer unit 36 digitizes analog signals and voltages to provide "real-time" telemetry intracardiac signals and battery elective replacement indicator (ERI) and end-of-life (EOL) functions.

A power-on-reset and elective replacement indicator (POR/ERI) circuit 37 functions as a means to reset circuitry and related functions to a default condition upon detection of a low battery condition, which will occur upon initial device power-up or will transiently occur in the presence of electromagnetic interference, for example. POR/ERI circuit 37 also functions to monitor the depth of discharge of battery 32, as will be hereinafter described in greater detail, and informs digital controller/timer circuit 31 when an ERI should be issued.

In particular, POR/ERI circuit 37 in accordance with the presently disclosed embodiment of the invention issues an ERI when the battery has reached a predetermined level of depletion. The parameters monitored by circuit 37 in order to determine the level of battery depletion can be different depending upon the particular implementation of the invention, and may involve, for example, one of the prior art impedance measurement schemes previously described.

The operating commands for controlling the timing of pacemaker 10 are coupled by bus 30 to digital controller/timer circuit 31 wherein digital timers, registers, and counters are employed to establish the overall escape interval of the pacemaker, as well as various refractory, blanking, and other timing windows for controlling the operation of the peripheral components within input/output circuit 22.

Digital controller/timer circuit 31 is coupled to sensing circuitry including a sense amplifier circuit 38 and a sensitivity control circuit 39. In particular, digital controller/timer circuit 31 receives an A-EVENT (atrial event) signal on line 40, and a V-EVENT (ventricular event) signal on line 41. Sense amplifier circuit 38 is coupled to leads 14 and 15, in order to receive the V-SENSE (ventricular sense) and A-SENSE (atrial sense) signals from heart 16. Sense amplifier circuit 38 asserts the A-EVENT signal on line 40 when an atrial event (i.e., a paced or intrinsic atrial event) is detected, and asserts the V-EVENT signal on line 41 when a ventricular event (paced or intrinsic) is detected. Sense amplifier circuit 38 includes one or more sense amplifiers corresponding, for example, to that disclosed in U.S. Pat. No. 4,379,459 issued to Stein on Apr. 12, 1983, incorporated by reference herein in its entirety.

Sensitivity control 39 is provided to adjust the gain of sense amplifier circuitry 38 in accordance with programmed sensitivity settings, as would be appreciated by those of ordinary skill in the pacing art.

A V-EGM (ventricular electrocardiogram) amplifier 42 is coupled to a conductor in lead 14 to receive a V-SENSE signal from heart 16. Similarly, an A-EGM (atrial electrocardiogram) amplifier 43 is coupled to one conductor of lead 15 to receive the A-SENSE signal from heart 16. The electrogram signals developed by V-EGM amplifier 42 and A-EGM amplifier 43 are used on those occasions when the implanted device is being interrogated by external programmer 11, to transmit by uplink telemetry a representation of the analog electrogram of the patient's electrical heart activity, such as described in U.S. Pat. No. 4,556,063, issued to Thompson et al., assigned to the assignee of the present invention and incorporated herein by reference.

Digital controller and timer circuit 31 is coupled to a charge pump circuit 44 via a plurality of control lines designated collectively as 45 in FIG. 1, and to a charge pump comparator 46 via a plurality of control lines 47. Also, circuit 31 is coupled to an output control circuit 48 via a plurality of lines designated as 49. Charge pump circuit 44 responds to signals from controller circuit 31 to initiate the charging of output capacitors therein, as will be hereinafter described in greater detail. In particular, and as will be described below in greater detail, charge pump circuit 44 includes atrial and ventricular hold capacitors (not shown in FIG. 1) for storage of charge for atrial and ventricular pacing pulses, respectively. The atrial capacitor's charge appears on an output line CAHOLD from charge pump circuit 44; the ventricular capacitor's charge appears on an output line CVHOLD from charge pump circuit 44. The atrial charge on CAHOLD is provided to charge pump comparator 46 and to output control circuit 48; the ventricular charge on CVHOLD is provided to charge control circuit 44 and to output control circuit 48.

Charge pump comparator 46 is activated in response to signals from controller circuit 31 on lines 47. When activated, charge pump comparator 46 monitors the voltage on the CAHOLD and/or CVHOLD lines and provides signals to controller circuit 31 indicative of the charging level of the atrial and ventricular hold capacitors.

Output control circuit 48 is responsive to signals from digital controller/timer circuit 31 on lines 49 to cause the voltage on the CAHOLD and CVHOLD lines to be applied to the patient's heart. In particular, output control circuit is coupled to receive the CAHOLD and CVHOLD voltages, and is also coupled to one or more of the conductors in each lead 14 and 15. Digital controller/timer circuit 31 provides signals on lines 49 to output control circuit 48 indicating whether unipolar or bipolar pacing has been selected for the atrial and ventricular chambers. Output control circuit 48 responds to these signals by coupling the appropriate lead conductors to establish the desired current path for pacing pulses. For example, if bipolar atrial pacing is selected, output control circuit 48 will function to couple the two leads of bipolar atrial lead 15 to the atrial hold capacitor, so that atrial pacing pulses are delivered between the two atrial electrodes. If unipolar atrial pacing is selected, output control circuit 48 functions to couple the unipolar pacing electrode on lead 15 and the pacemaker's conductive outer canister to the atrial hold capacitor, so that atrial pacing pulses are delivered between the atrial tip electrode and the canister, acting as a common electrode.

As would be appreciated by those of ordinary skill in the art, input/output circuitry will include decoupling circuitry for temporarily decoupling sense amplifier circuit 38, V-EGM amplifier 42 and A-EGM amplifier 43 from leads 14 and 15 when stimulating pulses are being delivered from output control circuit 48. For the sake of clarity, such decoupling circuitry is not depicted in FIG. 2.

While specific embodiments of sense amplifier circuitry and EGM amplifier circuitry have been identified herein, this is done for the purposes of illustration only. It is believed by the inventor that the specific embodiments of such circuits are not critical to the present invention so long as they provide means for generating a stimulating pulse and provide digital controller/timer circuit 31 with signals indicative of natural and/or stimulated contractions of the heart. It is also believed that those of ordinary skill in the art could chose from among the various well-known implementations of such circuits in practicing the present invention.

Digital controller/timer circuit 31 is coupled to an activity circuit 50 for receiving, processing, and amplifying activity signals received from activity sensor 20. A suitable implementation of activity circuit 50 is described in detail in the above-referenced Sivula et al. application. It is believed that the particular implementation of activity circuit 50 is not critical to an understanding of the present invention, and that various activity circuits are well-known to those of ordinary skill in the pacing art.

As previously noted, digital controller/timer circuit 31 includes certain registers for storing digital data used in the control of pacemaker functions. In the case of programmable functions, the digital data representing selected values for programmable parameters are downloaded from an external programming device to pacemaker 10 via the telemetry link. As would be appreciated by those of ordinary skill in the art, a downloaded digital value can contain bits identifying the parameter to be programmed and bits identifying the selected value for that parameter.

Figures 2, 3, 4:
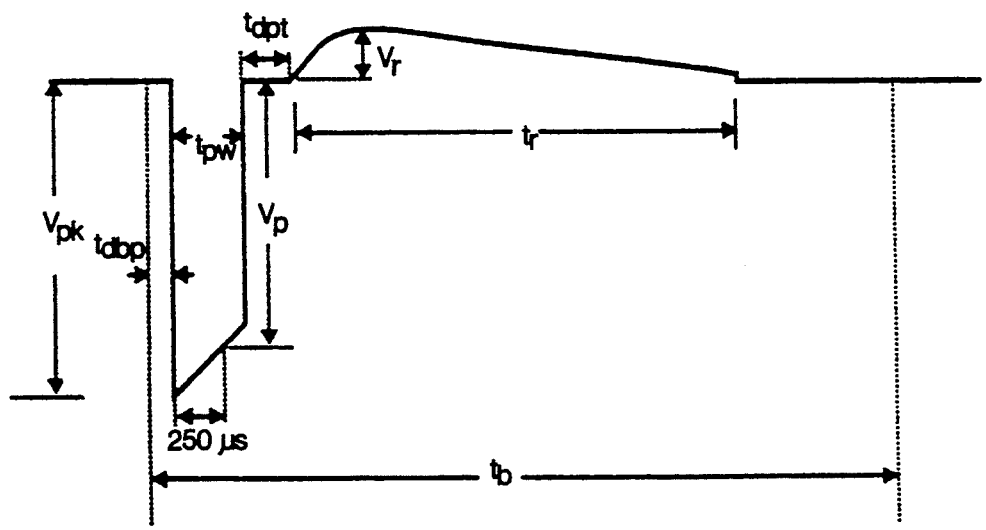
FIG. 2 is a diagram illustrating the format of an atrial output control register in the digital controller/timer circuit from FIG. 1.
FIG. 3 is a diagram illustrating the format of a ventricular output control register in the digital controller/timer circuit from FIG. 1.
FIG. 4 is an illustration of the morphology of a pacing pulse produced by the pacemaker of FIG. 1.

One of the registers maintained in digital controller/timer circuit 31 in accordance with the presently disclosed embodiment of the invention is an eight-bit atrial output control register. Digital controller/timer circuit 31 uses the data in the atrial output control register to control various aspects of atrial pacing by pacemaker 10. In FIG. 2, there is shown a diagram of the atrial output control register.

Referring to FIG. 2, the most significant bit (MSB) position of the atrial output control register, i.e., bit seven, is not used. Bit position six, designated AUNB, stores a binary value identifying whether unipolar or bipolar atrial pacing is to be performed. As would be appreciated by those of ordinary skill in the art, unipolar atrial pacing involves delivery of an atrial stimulating pulse between a tip electrode of a unipolar atrial lead and the conductive can of pacemaker 10, acting as a common electrode. Bipolar atrial pacing, on the other hand, involves delivery of an atrial stimulating pulse between the tip and ring electrodes of a bipolar atrial pacing lead. When bit six of the atrial output control register is a "1", unipolar atrial pacing is selected; when bit six is a "0", bipolar pacing is selected.

Bit position five of the atrial output control register, designated ACPD, stores a bit which enables and disables the atrial portion of charge pump circuit 44. When the ACPD bit is set to "1", the atrial portion of charge pump circuit 44 is disabled, resulting in 0-V atrial pacing pulses. When ACPD is a "0", the atrial portion of charge pump circuit 44 is enabled, so that atrial pulses of the programmed amplitude are generated.

Bit position four of the atrial output control register, designated AREG, stores a bit for enabling and disabling charge pump comparator 46, as will hereinafter be described in greater detail. When the AREG bit is a "0", the atrial output capacitor is charged in a normal fashion without the use of charge pump comparator 46 for monitoring the charge level. For the purposes of the following description, this type of charging will be referred to as "unregulated" charging. When the AREG bit is a "1", charge pump comparator 46 is enabled, such that the charging level of the atrial output capacitor is monitored to ensure that the selected output amplitude is reached. This will be referred to herein as "regulated" charging.

The low-order four bit positions (bit positions three through zero, designated AAS3, AAS2, AAS1 and AAS0 in FIG. 2) of the atrial output control register store a four-bit atrial amplitude value which determines the level to which the atrial output capacitor is charged and thus the amplitude of atrial stimulating pulses. The atrial amplitude value is interpreted in conjunction with the AREG bit; that is, the amplitude resulting from a given atrial amplitude value is different depending upon whether the charge amplitude control circuit is enabled or disabled. The four-bit atrial amplitude value is also interpreted in conjunction with a bit from a ventricular output control register, to be hereinafter described in greater detail. In particular, the state of one bit, VAS3 in the ventricular output control register affects the interpretation of the four-bit atrial amplitude value. The different atrial stimulating pulse amplitudes resulting from the various combinations of atrial amplitude values, AREG values, and VAS3 values are set forth in the following Table 1:

As shown in FIG. 3, the MSB position (bit seven) of the ventricular output control register is designated SAVB. The SAVB bit, when set to "1", allows charge pump circuit 44 to be disabled when a low power supply condition is detected, in order to conserve the remaining available power from battery 32. This bit is set to "1" by digital controller/timer circuit 31 when POR-/ERI circuit 37 detects a low power supply condition. When SAVB is "0", this power saving function is disabled.

Bit position six in the ventricular output control register, designated VUNB, selects either unipolar or bipolar ventricular pacing, just as the AUNB bit in the atrial

TABLE 1

| AAS3 | AAS2 | AAS1 | AAS0 | REGULATED AMPLITUDE (AREG = 1) | LOW UN-REGULATED AMPLITUDE (AREG = 0, AAS3 = 0, VAS3 = 0) | HIGH UN-REGULATED AMPLITUDE (AREG = 0, VAS3 = 1) |
|---|---|---|---|---|---|---|
| 0 | 0 | 0 | 0 | 0.5 | 1.25 | 2.5 |
| 0 | 0 | 0 | 1 | 1.0 | 1.25 | 2.5 |
| 0 | 0 | 1 | 0 | 1.5 | 2.50 | 5.0 |
| 0 | 0 | 1 | 1 | 2.0 | 2.50 | 5.0 |
| 0 | 1 | 0 | 0 | 2.5 | 3.75 | 5.0 |
| 0 | 1 | 0 | 1 | 3.0 | 3.75 | 5.0 |
| 0 | 1 | 1 | 0 | 3.5 | 5.00 | 7.5 |
| 0 | 1 | 1 | 1 | 4.0 | 5.00 | 7.5 |
| 1 | 0 | 0 | 0 | 4.5 | N/A | 7.5 |
| 1 | 0 | 0 | 1 | 5.0 | N/A | 7.5 |
| 1 | 0 | 1 | 0 | 5.5 | N/A | 7.5 |
| 1 | 0 | 1 | 1 | 6.0 | N/A | 7.5 |
| 1 | 1 | 0 | 0 | 6.5 | N/A | 7.5 |
| 1 | 1 | 0 | 1 | 7.0 | N/A | 7.5 |
| 1 | 1 | 1 | 0 | 7.5 | N/A | 7.5 |
| 1 | 1 | 1 | 1 | 8.0 | N/A | 7.5 |

The "N/A"("not available") entries in the "low unregulated amplitude" column of Table 1 above reflect the fact that in the presently disclosed embodiment of the invention, the low unregulated amplitudes are available only when AAS3 and VAS3 are both zero; if either atrial or ventricular pacing pulses of greater than or equal to 4.5-V are to be delivered, only the "high unregulated amplitude" settings are available. Stated differently, "high unregulated amplitude" atrial settings are used if either AAS3 or VAS3 is a "1".

As noted above, a second register maintained in digital controller/timer circuit 31, called the ventricular output control register, is used to control various aspects of ventricular output pulse generation, in a manner analogous to the atrial output control register. The format of the ventricular output control register is depicted in FIG. 3.

output control register selected the mode of atrial pacing.

Bit position five in the ventricular output control register, designated VCPD, is used to enable and disable the ventricular portion of charge pump circuit 44.

The remaining four bit positions in the ventricular output control register, designated VAS3, VAS2, VAS 1, and VAS0, store a four-bit ventricular amplitude value corresponding to the programmably selected ventricular amplitude. The four-bit ventricular amplitude value is interpreted in conjunction with the VREG bit and the AAS3 bit, just as the atrial amplitude value is interpreted in conjunction with the AREG and VAS3 bits. The different ventricular stimulating pulse amplitudes resulting from the various combinations of ventricular amplitude values, VREG values, and AAS3 values are set forth in the following Table 2:

TABLE 2

| VAS3 | VAS2 | VAS1 | VAS0 | REGULATED AMPLITUDE (VREG = 1) | LOW UN-REGULATED AMPLITUDE (VREG = 0, AAS3 = 0, VAS3 = 0) | HIGH UN-REGULATED AMPLITUDE (AREG = 0, AAS3 = 1) |
|---|---|---|---|---|---|---|
| 0 | 0 | 0 | 0 | 0.5 | 1.25 | 2.5 |
| 0 | 0 | 0 | 1 | 1.0 | 1.25 | 2.5 |
| 0 | 0 | 1 | 0 | 1.5 | 2.50 | 5.0 |
| 0 | 0 | 1 | 1 | 2.0 | 2.50 | 5.0 |
| 0 | 1 | 0 | 0 | 2.5 | 3.75 | 5.0 |
| 0 | 1 | 0 | 1 | 3.0 | 3.75 | 5.0 |
| 0 | 1 | 1 | 0 | 3.5 | 5.00 | 7.5 |
| 0 | 1 | 1 | 1 | 4.0 | 5.00 | 7.5 |
| 1 | 0 | 0 | 0 | 4.5 | N/A | 7.5 |
| 1 | 0 | 0 | 1 | 5.0 | N/A | 7.5 |

TABLE 2-continued

| VAS3 | VAS2 | VAS1 | VAS0 | REGULATED AMPLITUDE (VREG = 1) | LOW UN-REGULATED AMPLITUDE (VREG = 0, AAS3 = 0, VAS3 = 0) | HIGH UN-REGULATED AMPLITUDE (AREG = 0, AAS3 = 1) |
|---|---|---|---|---|---|---|
| 1 | 0 | 1 | 0 | 5.5 | N/A | 7.5 |
| 1 | 0 | 1 | 1 | 6.0 | N/A | 7.5 |
| 1 | 1 | 0 | 0 | 6.5 | N/A | 7.5 |
| 1 | 1 | 0 | 1 | 7.0 | N/A | 7.5 |
| 1 | 1 | 1 | 0 | 7.5 | N/A | 7.5 |
| 1 | 1 | 1 | 1 | 8.0 | N/A | 7.5 |

As with the atrial amplitude value, the "N/A" entries in the "low unregulated amplitude" column of Table 2 reflect the fact that if either VAS3 or AAS3 are set to "1", only "high unregulated amplitude" values are available.

Although "regulated" and "unregulated" atrial and ventricular output amplitudes may be selected by digital controller/timer circuit 31 by setting the AREG and VREG bits, in the presently preferred embodiment of the invention selection of "regulated" or "unregulated" output is not a programmable parameter that may be selected through the use of an external programmer. The selection of "regulated" or "unregulated" output is done automatically by pacemaker 10, as will be hereinafter explained in greater detail. Thus, for each chamber, there are sixteen possible amplitude settings, numbered zero through fifteen: OFF, and 0.5-V to 7.5-V in 0.5-V increments.

As will be appreciated by those of ordinary skill in the art, the application of a stimulating pulse to one chamber of the heart is a multiple-step process. The process is initiated by digital controller/timer circuit 31 in response to a predetermined set of conditions. For example, controller/timer circuit 31 may function to initiate delivery of a ventricular pacing pulse only when a predetermined time interval elapses following a paced or natural atrial event, when no natural ventricular event is detected during that time period. It is believed that the details of the pacing algorithm, i.e., the various conditions, time intervals, algorithms, and the like that define the pacing functions of pacemaker 10, are not critical to an understanding of the present invention, and will not be described herein in substantial detail. It is believed that various pacing algorithms and implementations of pacemakers are known and/or commercially available, and that the present invention may be readily adapted for use in different systems by persons having the benefit of the present disclosure. For the purposes of the present disclosure, it is sufficient to state that digital controller/timer circuit 31 implements a pacing algorithm and at various times takes steps to initiate delivery of atrial and/or ventricular stimulating pulses.

When controller/timer circuit 31 initiates delivery of a pacing pulse, it asserts one or more signals conducted on lines 45 to initiate the charging of the appropriate (i.e., atrial or ventricular) output capacitor in charge pump circuit 44. As noted above, and in accordance with one aspect of the present invention, the charging of output capacitors by charge pump circuit 44 may or may not also involve activation of charge pump comparator 46. If charge pump comparator 46 is required, it is activated by one or more signals asserted on lines 47—for example, signals derived from the AREG and-/or VREG bits in the atrial and ventricular output control registers may be provided to activate charge pump comparator 46.

The charging phase, which will be described below in greater detail, results in a voltage stored on so-called pump capacitors in charge pump circuit. After the pump capacitors are charged, digital controller/timer circuit 31 issues control signals causing charge pump circuit to begin a pumping phase, wherein charge on the pump capacitors is transferred to an output, or "hold" capacitor. The level of voltage stored on the hold capacitor will then reflect the output amplitude value (atrial or ventricular) stored in the low-order four bits of the corresponding output control register. The stored voltage level will also reflect whether "regulated" or "unregulated" charging is performed. In the case of "regulated" charging, during the pumping phase the voltage on the hold capacitor is applied (via either the CAHOLD or VAHOLD line) to charge pump comparator 46, which asserts an output signal only when the stored voltage reaches the desired level, measured in multiples of a 1.2-V reference voltage that is also applied to charge control circuit. The output from charge control circuit is provided to control circuit 31, which responds to the charge control signal to stop the pumping phase. In the case of "unregulated" charging, charge pump comparator 46 is not activated, and the voltage established on the output capacitor is proportional to the output voltage from battery 32. The manner in which this is accomplished will be described in greater detail below.

After the desired voltage has been stored on the pump capacitors and then pumped onto the desired output capacitor, digital controller/timer circuit 31 asserts the appropriate signals on lines 49 to cause the output capacitor to be momentarily coupled to the appropriate conductor(s) of one of the leads 14 or 15. In FIG. 4, there is shown a waveform of a typical pacing pulse delivered to the patient's heart. Note from FIG. 4 that it is actually a negative-going voltage pulse that is applied. The peak (i.e., most negative) pacing pulse voltage is designated in FIG. 4 as $V_{pk}$. The width of the pulse, which corresponds to the time interval during which the hold capacitor is coupled to the pacing leads, is designated as $t_{pw}$. The pacing pulse "amplitude", which corresponds to the settings of Tables 1 and 2 above, is designated as $V_p$ in FIG. 4. Note that the pulse amplitude $V_p$ is measured at a point 250-μSec after the beginning of the pacing pulse.

Figure 5:
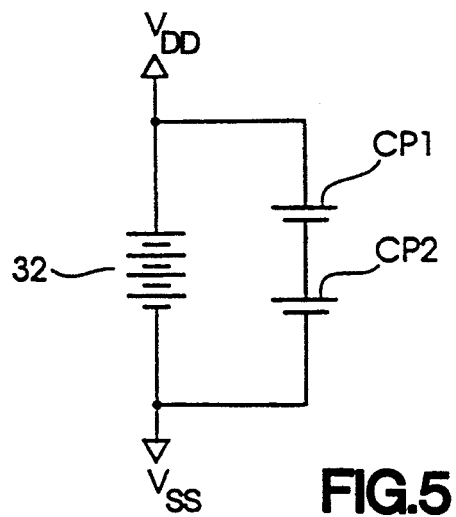
FIG. 5 is a schematic diagram of a pump capacitor series charging circuit in accordance with the disclosed embodiment of the invention.

Turning now to FIG. 5, there is shown a circuit illustrating one configuration of charge pump circuit during the charging phase. As will hereinafter be further explained with reference to later Figures, charge pump circuit 44 is a versatile circuit which is responsive to various combinations of control signals to achieve different configurations of components therein. Thus, the circuit of FIG. 5 is an equivalent circuit showing how charge pump circuit 44 operates in one instance. In particular, the configuration of FIG. 5 depicts the state of charge pump circuit 44 during one type of charge phase, called a "serial charge".

The circuit of FIG. 5 includes two pump capacitors, designated CP1 and CP2. Capacitors CP1 and CP2 are, in the configuration of FIG. 5, coupled in series between the terminals of battery 32, so that one-half of the battery voltage is stored on each capacitor CP1 and CP2.

Figure 6:
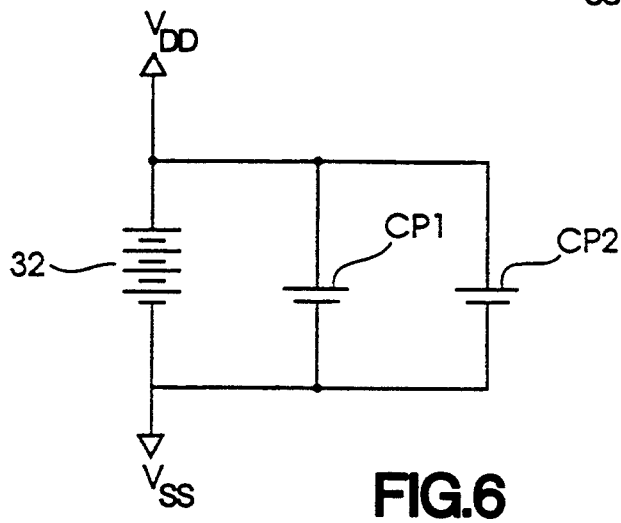
FIG. 6 is a schematic diagram of a pump capacitor parallel charging circuit in accordance with the disclosed embodiment of the invention.

In FIG. 6, there is shown a circuit illustrating another possible configuration of charge pump circuit 44 during the charging phase. The configuration of FIG. 6 is called a "parallel charge", in which pump capacitors CP1 and CP2 are coupled in parallel between the terminals of battery 32. With the configuration of FIG. 6, the entire battery voltage is stored on each capacitor CP1 and CP2.

Figure 7:
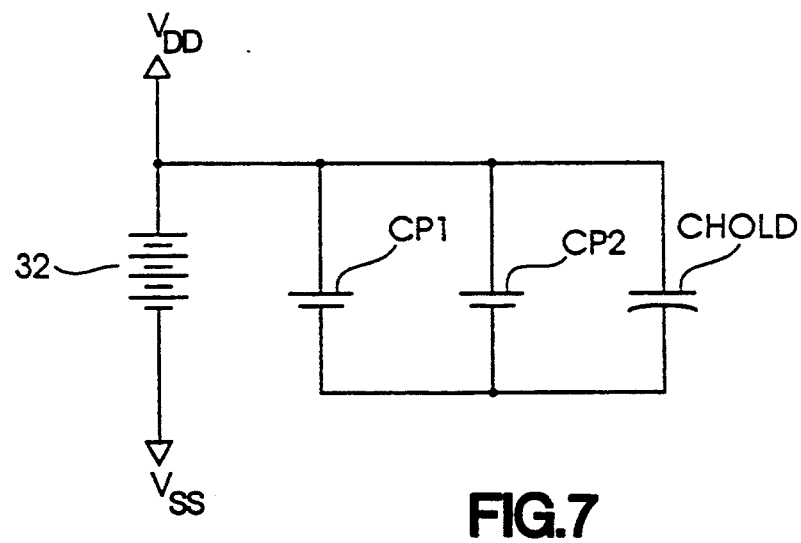
FIG. 7 is a schematic diagram of a parallel charge pump circuit in accordance with the disclosed embodiment of the invention.

Turning now to FIG. 7, there is shown a circuit for one possible configuration of charge pump circuit 44 during the pumping phase, during which phase charge previously stored on pump capacitors CP1 and CP2 during the charge phase are applied to a hold capacitor, designated as CHOLD in FIG. 7. It is to be understood that hold capacitor CHOLD in FIG. 7 may be either the atrial hold capacitor CAHOLD or the ventricular hold capacitor CVHOLD, as will hereinafter become more apparent. The pumping circuit configuration of FIG. 7 will be hereinafter referred to as a "parallel $V_{DD}$" arrangement, since the pumping capacitors are coupled in parallel to the positive ($V_{DD}$) terminal of battery 32.

Figure 8:
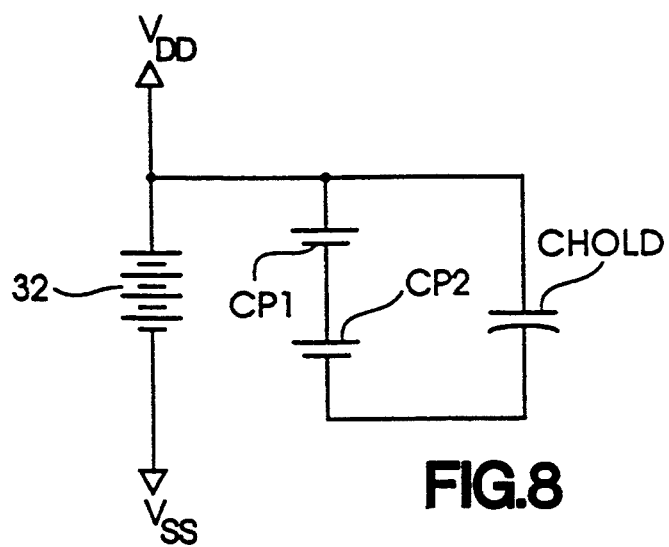
FIG. 8 is a schematic diagram of a series charge pump circuit in accordance with the disclosed embodiment of the invention.

In FIG. 8, there is shown a circuit for another possible configuration of charge pump circuit 44 during the pumping phase. Again, capacitor CHOLD in FIG. 8 may be either the atrial hold capacitor CAHOLD or the ventricular hold capacitor CVHOLD. The pumping circuit configuration of FIG. 8 will be hereinafter referred to as a "series $V_{DD}$" arrangement.

Figure 9:
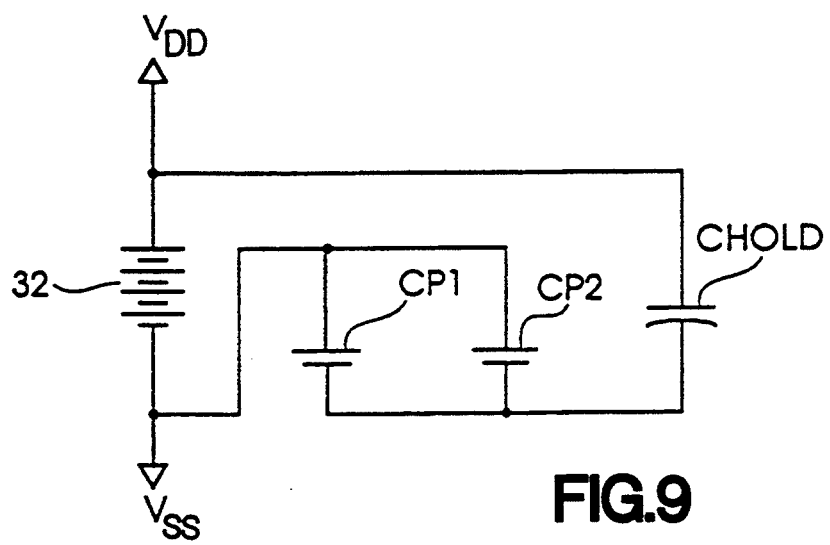
FIG. 9 is a schematic diagram of another parallel charge pump circuit in accordance with the disclosed embodiment of the invention.

In FIG. 9, there is shown a circuit for still another possible configuration of charge pump circuit 44 during the pumping phase, wherein capacitor CHOLD may be either the atrial or ventricular hold capacitor. The pumping arrangement of FIG. 9 will be hereinafter referred to as a "parallel $V_{SS}$" arrangement, since the pump capacitors CP1 and CP2 are coupled in parallel to the negative ($V_{SS}$) terminal of battery 32.

Figure 10:
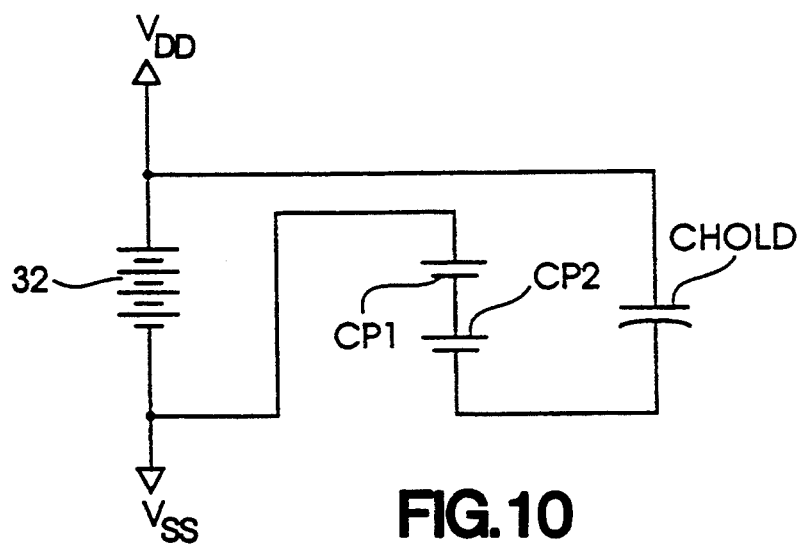
FIG. 10 is a schematic diagram of another series charge pump circuit in accordance with the disclosed embodiment of the invention.

Finally, in FIG. 10, there is shown a circuit for another possible configuration of charge pump circuit 44 during the pumping phase. The pumping arrangement of FIG. 10 will be hereinafter referred to as a "series $V_{SS}$" arrangement.

As will be appreciated by those of ordinary skill in the circuit art, with the two possible charging configurations, parallel and serial, and the four possible pumping configurations, parallel and serial $V_{DD}$ and parallel and serial $V_{SS}$, there are eight possible charge/pump sequences which can be performed, each resulting in a different charge being pumped onto the hold capacitor. In the following Table 3, there is set forth the eight holding capacitor voltages which can be achieved with the eight different possible charge/pump sequences:

TABLE 3

| CHARGING MODE | PUMPING MODE | HOLDING CAPACITOR VOLTAGE |
| --- | --- | --- |
| SERIES | PARALLEL $V_{DD}$ | $1/2 \times V_{DD}$ |
| SERIES | SERIES $V_{DD}$ | $V_{DD}$ |
| SERIES | PARALLEL $V_{SS}$ | $3/2 \times V_{DD}$ |
| SERIES | SERIES $V_{SS}$ | $2 \times V_{DD}$ |
| PARALLEL | PARALLEL $V_{DD}$ | $1 \times V_{DD}$ |
| PARALLEL | SERIES $V_{DD}$ | $2 \times V_{DD}$ |
| PARALLEL | PARALLEL $V_{SS}$ | $2 \times V_{DD}$ |
| PARALLEL | SERIES $V_{SS}$ | $3 \times V_{DD}$ |

Figure 11:
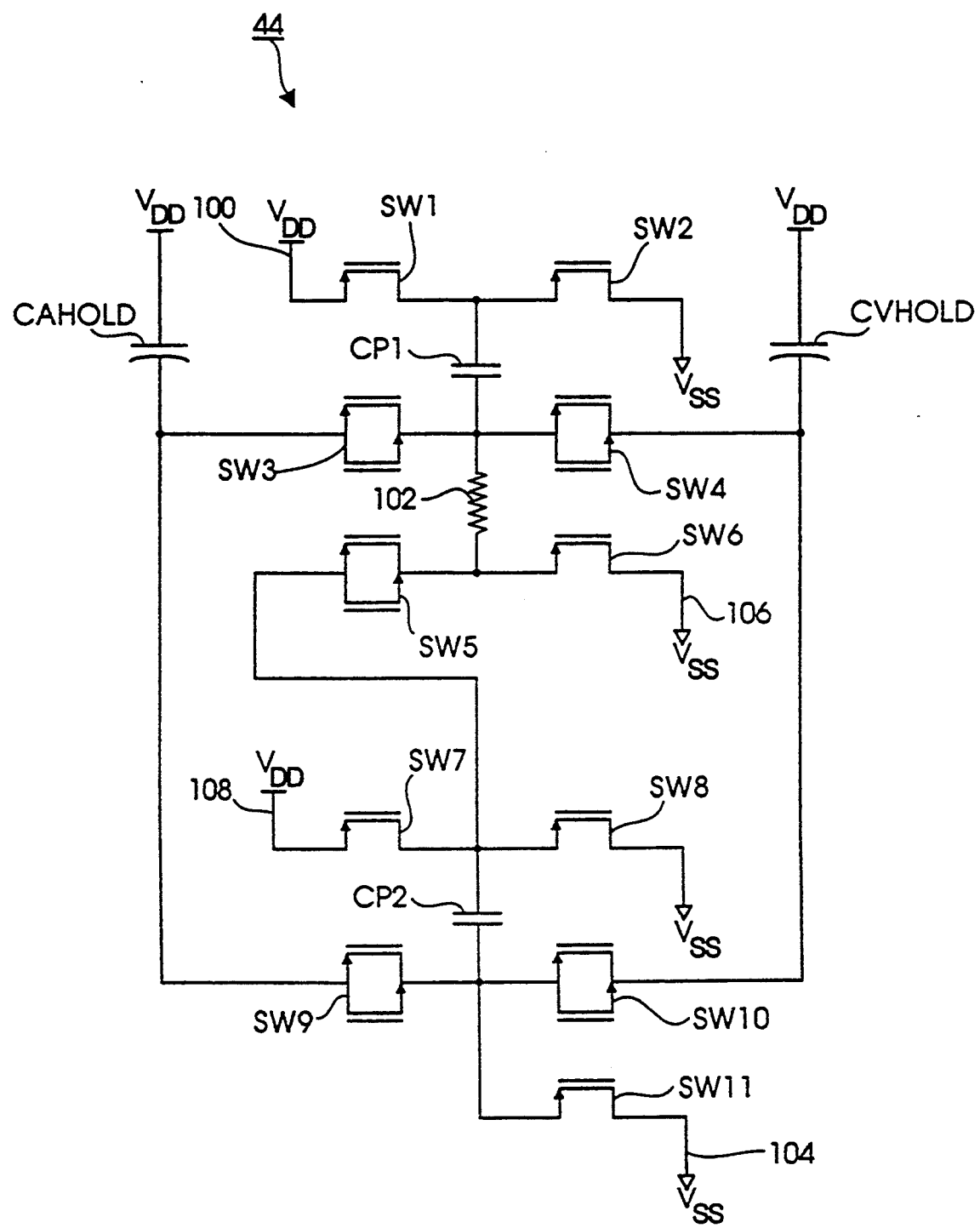
FIG. 11 is a schematic diagram of the charge pump circuit in the pacemaker of FIG. 1.

Turning now to FIG. 11, there is shown a schematic diagram of charge pump circuit 44 in accordance with the presently disclosed embodiment of the invention. The circuit of FIG. 11 includes the two pumping capacitors CP1 and CP2 and the two hold capacitors CAHOLD and CVHOLD. As will be appreciated by those of ordinary skill in the art, the circuit of FIG. 11 is capable of charging the two pumping capacitors CP1 and CP2 in either the parallel or serial modes described above, and is additionally capable of pumping both the CAHOLD and CVHOLD capacitors in any of the four charging modes (parallel and serial $V_{DD}$ and $V_{SS}$). The different charge/pump sequences are controlled by means of the various switches in the circuit of FIG. 11, which switches are actuated by control signals provided to charge pump circuit 44 on lines 45 (see FIG. 1) from digital controller/timer circuit 31. It is to be understood that in the Figures, references to $V_{DD}$ represent connections to the positive terminal of battery 32 while references to $V_{SS}$ represent connections to the negative terminal of battery 32.

Charge pump circuit 44 of FIG. 11 includes a plurality of switches, designated as SW1 through SW 11, which in the presently preferred embodiment of the invention are implemented as simple FET devices. Although it is not shown in FIG. 11, switches SW1 through SW11 are controlled (i.e., opened and closed) in response to control signals provided from digital controller/timer circuit 31. In particular, digital controller/timer circuit 31 controls charge pump circuit 44 with a four phase clock sequence to (1) charge pump capacitors CP1 and CP2; (2) pump atrial hold capacitor CAHOLD; (3) charge pump capacitors CP1 and CP2; and (4) pump ventricular hold capacitor CVHOLD.

In charging phases one and three, switches SW1 through SW11 are configured by controller circuit 31 to charge pump capacitors CP1 and CP2 in either the series or parallel charging mode, depending upon the voltages to be developed on the respective atrial and ventricular hold capacitors CAHOLD and CVHOLD. For example, if series charging is required during clock phases one or three, controller circuit 31 actuates (closes) switches SW1, SW5, and SW11. This establishes a path beginning at the $V_{DD}$ connection designated as 100 in FIG. 11, through switch SW1, across capacitor CP1, through a 40-Ω resistor designated as 102 in FIG. 11, through switch SW5, across capacitor CP2, and then through switch SW11 to the $V_{SS}$ connection designated as 104. As will be appreciated by those of ordinary skill in the art, the configuration just described corresponds to the serial charging arrangement previously described with reference to FIG. 5.

If parallel charging is required during phases one or three of the charge pump sequence, controller circuit 31 asserts control signals to actuate (close) switches SW1, SW6, SW7, and SW11. With this switch configuration, a first charging path is established beginning at $V_{DD}$ connection 100, through pump capacitor CP1 and resistor 102, and then through switch SW6 to a $V_{SS}$ connection designated as 106 in FIG. 11. A second path is established beginning at a $V_{DD}$ connection designated as 108 and extending through switch SW7, pump capacitor CP2, and through switch SW11 to $V_{SS}$ connection 104. This configuration of switches results in the parallel charging arrangement previously described with reference to FIG. 5, in which pump capacitors CP1 and CP2 are coupled in parallel between the positive and negative terminals of battery 32.

In charging phases two and four, switches SW1 through SW11 are operated to pump the atrial (phase two) and ventricular (phase four) hold capacitors CAHOLD and CVHOLD, respectively. Again, switches SW1 through SW11 are selectively actuated by control signals issued by controller circuit 31.

The four different pumping modes (parallel and series $V_{DD}$ and $V_{SS}$) are accomplished through the actuation of different combinations of switches SW1 through SW11, as set forth in the following Table 4:

TABLE 4

| PUMPING MODE | CAPACITOR TO CHARGE | SWITCHES ACTUATED (CLOSED) |
|---|---|---|
| PARALLEL $V_{DD}$ | CAHOLD | SW1, SW3, SW7, SW9 |
| SERIES $V_{DD}$ | CAHOLD | SW1, SW5, SW9 |
| PARALLEL $V_{SS}$ | CAHOLD | SW2, SW3, SW8, SW9 |
| SERIES $V_{SS}$ | CAHOLD | SW2, SW5, SW9 |
| PARALLEL $V_{DD}$ | VAHOLD | SW1, SW4, SW7, SW10 |
| SERIES $V_{DD}$ | VAHOLD | SW1, SW5, SW10 |
| PARALLEL $V_{SS}$ | VAHOLD | SW2, SW4, SW8, SW10 |
| SERIES $V_{SS}$ | VAHOLD | SW2, SW5, SW10 |

As will be appreciated by those of ordinary skill in the circuit art, each of the switches SW1 through SW11 in charge pump circuit 44 of FIG. 11 has an impedance associated therewith, as set forth in the following Table 5:

TABLE 5

| SWITCH | IMPEDANCE |
|---|---|
| SW1 | 550-Ω |
| SW2 | 550-Ω |
| SW3 | 4700-Ω |
| SW4 | 4700-Ω |
| SW5 | 720-Ω |
| SW6 | 900-Ω |
| SW7 | 565-Ω |
| SW8 | 4365-Ω |
| SW9 | 925-Ω |
| SW10 | 925-Ω |
| SW11 | 925-Ω |

The switch impedances listed in Table 5 are preferably selected such that when pacemaker 10 is operating at 400 beats per minute (BPM) there is at most a 25% pacing pulse amplitude loss and when pacemaker 10 is operating at 180-BPM there is at most a 10% amplitude loss, for a supply voltage of 2-V. The impedances were also chosen such that there is a minimum possible current drain resulting from operation of charge pump circuit 44. It should be noted that the time constants for charging and pumping are relatively large with respect to the time allowed for charge transfer. In particular, each phase of the four phase sequence established by controller circuit 31 lasts for 244- μSec, so that only 244-μSec is available for each charge transfer. This means that charge transfer is not completed in each phase of the four phase charge/pump sequence. The maximum total switch impedance which results from each of the series and parallel charging and pumping configurations, along with the minimum percentage of charge transfer is set forth in the following Table 6:

TABLE 6

| | MAXIMUM EQUIVALENT RESISTANCE | MAXIMUM EQUIVALENT CAPACITANCE | MINIMUM CHARGE TRANSFER |
|---|---|---|---|
| SERIES CHARGE | 2235-Ω | 0.055-μF | 86% |
| PARALLEL CHARGE | 1490-Ω | 0.220-μF | 52% |
| SERIES PUMP | 2235-Ω | 0.055-μF | 86% |
| PARALLEL PUMP | 2645-Ω | 0.220-μF | 34% |

Due to the incomplete charge transfer during the charging phase, there is some interaction between atrial and ventricular holding capacitors. This results in a slightly decreased pacing amplitude in cases where there is a short A-V interval or a short V-A interval in the pacing cycle. It is believed that for worst-case A-V interaction, however, the maximum ventricular amplitude loss is less than 5%. As previously discussed with reference to FIGS. 2 and 3, atrial and ventricular output operation is controlled according to bits in an atrial output control register and a ventricular output control register. In particular, the bits of these registers defined the charging and pumping configurations to be used. The series charging mode (FIG. 5) is used if VAS3 and AAS3 are both low; this corresponds to "unregulated" output amplitude choices of $\frac{1}{2} \times V_{DD}$, $V_{DD}$, $3/2 \times V_{DD}$, or $2 \times V_{DD}$. If VAS3 or AAS3 is high, the parallel charging mode is used; this corresponds to either atrial or ventricular pacing amplitude set to $3 \times V_{DD}$. For this case the "unregulated" output amplitude choices are $1 \times V_{DD}$, $2 \times V_{DD}$, or $3 \times V_{DD}$. The possibility of charging the pump capacitors differently for atrial and ventricular pumping cycles is deliberately eliminated in the presently preferred embodiment of the invention, to prevent excessive current drain. If different modes for atrial and ventricular charging were allowed, the wasted current would be on the order of 300-μA.

The pumping modes for ventricular and atrial hold capacitors CVHOLD and CAHOLD are determined by AS3, AS2, and AS1 according to the following Table 7:

TABLE 7

| VAS3 OR AAS3 | AS3 | AS2 | AS1 | CHARGING MODE | PUMPING MODE | AMPLITUDE |
|---|---|---|---|---|---|---|
| 0 | 0 | 0 | 0 | SERIES | PARALLEL $V_{DD}$ | $1/2 \times V_{DD}$ |

TABLE 7-continued

| VAS3 OR AAS3 | AS3 | AS2 | AS1 | CHARGING MODE | PUMPING MODE | AMPLITUDE |
|---|---|---|---|---|---|---|
| 0 | 0 | 0 | 1 | SERIES | SERIES $V_{DD}$ | $1 \times V_{DD}$ |
| 0 | 0 | 1 | 0 | SERIES | PARALLEL $V_{SS}$ | $3/2 \times V_{DD}$ |
| 0 | 0 | 1 | 1 | SERIES | SERIES $V_{SS}$ | $2 \times V_{DD}$ |
| 1 | 0 | 0 | 0 | PARALLEL | PARALLEL $V_{DD}$ | $1 \times V_{DD}$ |
| 1 | 0 | 0 | 1 | PARALLEL | SERIES $V_{DD}$ | $2 \times V_{DD}$ |
| 1 | 0 | 1 | 0 | PARALLEL | PARALLEL $V_{SS}$ | $2 \times V_{DD}$ |
| 1 | 0 | 1 | 1 | PARALLEL | SERIES $V_{SS}$ | $3 \times V_{DD}$ |
| 1 | 1 | X | X | PARALLEL | SERIES $V_{SS}$ | $3 \times V_{DD}$ |

Figure 12:
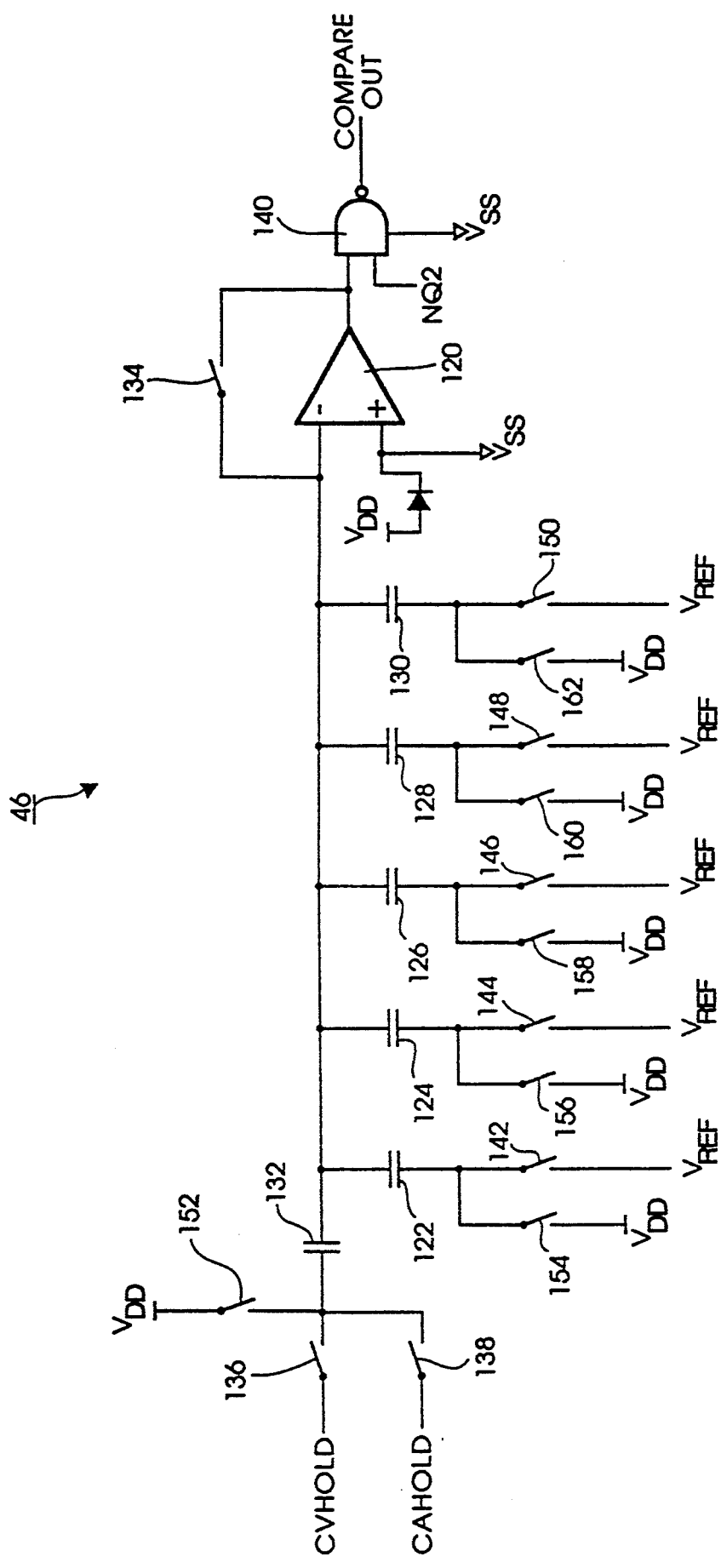
FIG. 12 is a schematic diagram of the charge pump comparator in the pacemaker of FIG. 1.

Turning now to FIG. 12, there is shown a schematic diagram of charge pump comparator 46 previously discussed with reference to FIG. 1. Charge pump comparator 46 is used to set "regulated" pacing amplitudes, by determining when the atrial and ventricular hold capacitors CAHOLD and CVHOLD have been pumped to the programmed amplitude, and then shutting off the charge pumps. Charge pump comparator 46 uses a switch capacitor digital-to-analog converter circuit referenced to a reference voltage $V_{REF}$ provided from $V_{REF}$ and bias circuit 35. Charge pump comparator 46 includes a differential amplifier 120 to compare the programmed amplitude to the voltage on the hold capacitor at the end of each atrial and ventricular charge pumping phase. Charge pump comparator 46 effectively has 16 thresholds spaced in 0.571-V increments, resulting in 0.5-V increments for regulated pacing amplitudes when the amplitude is measured from tip-to-ring on a bipolar lead or tip-to-case on a unipolar lead, 250-μSec from the falling edge of the negative-going pulse, as previously described with reference to FIG. 4. Programming the amplitude select bits in the atrial and ventricular output control registers sets the comparator threshold.

In addition to differential amplifier 120, charge pump comparator comprises an array of binary-weighted capacitors 122, 124, 126, 128, and 130, and an input capacitor 132. Capacitor 122 has a capacitance that is twice that of capacitor 124. Capacitor 124, in turn, has a capacitance twice that of capacitor 126, which has a capacitance twice that of capacitor 128. Capacitors 128 and 130 have the same capacitance. A switch 136 operates to selectively connect the CVHOLD capacitor from charge pump circuit 44 to charge pump comparator 46, while a switch 138 operates to a selectively connect the CAHOLD capacitor to charge pump comparator. When either CAHOLD or CVHOLD is coupled to charge pump comparator 46, the voltage thereon is applied to the top plates of all of the binary-weighted capacitors 122, 124, 126, 128, and 130.

A switch 134 is coupled between the inverting input and output of differential amplifier 120. During the first of the four charge/pump sequence phases (i.e., the pump capacitor charging phase), switch 134 is closed, to zero the comparator by eliminating any charge left over from a previous comparison. Closing switch 134 also reduces the effects of offset in the first stage of the comparator.

The output from differential amplifier is coupled to one input of a NAND gate 140, the other input of which being coupled to receive a signal NQ2 from controller circuit 31. The signal NQ2 is at a high logic level whenever switch 134 is not closed. The output of NAND gate 140, designated COMPARE OUT in FIG. 12, is the output signal produced by charge pump comparator 46. The COMPARE OUT signal is provided to controller/timer circuit 31 to provide an indication of the results of comparisons performed by comparator 46. The non-inverting input of differential amplifier 120 receives a voltage that is one diode drop below $V_{DD}$. Thus, when switch 134 is closed to zero the array, the voltage on the top plates of all of the binary-weighted capacitors 122, 124, 126, 128, and 130 is driven to a voltage of about 0.5-V below $V_{DD}$. Also while switch 134 is closed, the bottom plates of all of the binary-weighted capacitors 122, 124, 126, 128, and 130 are coupled, via switches 142, 144, 146, 148, and 150, respectively, to the reference voltage $V_{REF}$. Additionally, while switch 134 is closed, the bottom plate of input sampling capacitor 132 is coupled, via a switch 152, to $V_{DD}$.

Charge pump comparator 46 operates under control of a plurality of signals provided on lines 47 from controller circuit 31. During the atrial hold capacitor pumping phase, switch 134 is opened, and the bottom plate of input capacitor 1132 is coupled, by closing switch 138, to the CAHOLD capacitor. This causes a negative shift in voltage on the top plate of capacitor 134 which is proportional to the voltage on CAHOLD. A short time later, some of the bottom plates of the binary-weighted capacitors are coupled $V_{DD}$, via some combination of switches 154, 156, 158, 160, and 162, causing a positive shift in the voltage on the top plates thereof which is proportional to the amplitude code in the atrial output control register. In particular, the capacitors whose bottom plates are coupled to $V_{DD}$ is determined by the amplitude code, as would be appreciated by those of ordinary skill in the circuit art.

Charge pump comparator then determines whether the net change in voltage on the top plate is positive or negative with respect to the value on CAHOLD at the end of the pumping phase. If the voltage is negative, then the voltage across CAHOLD is larger than the programmed amplitude and the COMPARE OUT signal will be at a low logic level. This indicates to controller circuit 31 that charge pumping for the atrial side should be disabled. The COMPARE OUT signal is latched by digital controller/timer circuit 31 at the end of each pump cycle, before switch 134 is closed again to zero the array in preparation for another comparison.

A small amount of hysteresis can be provided by coupling a small metal-to-poly capacitor between the input and output of comparator 46. This provides approximately 1.1-mV of hysteresis at the input, and forces the comparator output to sit at one of the lower power supply rails, lowering current drain at the output of comparator 46.

Comparison for the CVHOLD capacitor is performed exactly as described for CAHOLD, except that it occurs during the fourth of the four charge/pump sequence phases.

Charge pump comparator 46 is also used when a new amplitude is first programmed into the atrial or ventricular output control registers. Programming a new atrial or ventricular amplitude causes the charge pumps in charge pump circuit 44 to be shut off and starts a discharge of the appropriate hold capacitor. Charge pump comparator 46 monitors the hold capacitor voltage to determine when it drops below the programmed value. When this occurs, the discharge is discontinued and the charge pumps are restarted.

In accordance with the presently disclosed embodiment of the invention, "unregulated" amplitudes are obtained by not using charge pump comparator 46 to shut off the charge pumps. The charge pumps are allowed to run continuously, resulting in the maximum possible amplitude for each of the pumping modes. It is to be understood that charge pump comparator 46 is still used when a new amplitude is programmed.

"Regulated" pacing amplitudes will begin to degrade when the supply voltage from battery 32 gets small enough to prevent charge pump circuit 44 from being able to charge the hold capacitors to programmed threshold of comparator 46. When this happens, the "regulated" pacing amplitudes will begin tracking the "unregulated" amplitudes. For "regulated" amplitudes less than or equal to 6-V, the "regulated" voltages will not begin to droop until the battery voltage drops below approximately 2.3-V.

Having described charge pump circuit 44 and charge pump comparator 46 in some detail, operation of pacemaker 10 in accordance with the presently disclosed embodiment of the invention will now be generally described. As noted above, pacemaker 10 in accordance with the presently disclosed embodiment of the invention offers ten programmable pacing pulse amplitude settings: 0.5-, 1.0-, 1.5-, 2.0-, 2.5-, 3.0-, 3.5-, 4.0-, 5.0-, and 7.5-V. In accordance with one feature of the presently disclosed embodiment, some of the programmable amplitudes are implemented as "regulated" settings for which charge pump comparator 46 is used to ensure that output pulses are generated at the desired amplitude. In the presently preferred embodiment of the invention, the 0.5- to 2.0-V, 3.0- and 4.0-V settings are implemented as "regulated" settings. Since these settings are "regulated", pacing pulses at these amplitude settings are delivered at a stable amplitude until the voltage from battery 32 declines from its beginning-of-life (BOL) level of 2.75- to 2.8-V, to around 2.0- to 2.3-v.

The remaining settings in the presently preferred embodiment of the invention (2.5-, 3.5-, 5.0- and 7.5-V) are implemented as "unregulated" amplitudes, for which charge pump comparator 46 is not activated. These "unregulated" settings are more current-efficient, since the additional current drain of charge pump comparator 46 is eliminated, but have the characteristic that the delivered amplitude with these settings declines in proportion with the decline in battery voltage.

In pacemaker 10, POR/ERI circuit 37 issues an elective replacement indicator (ERI) when it detects that battery 32 is at least one-third depleted and that battery voltage has dropped to a consistent level of approximately 2.6-V. Although these are the presently preferred ERI criteria, it is contemplated that various other indicia of ERI may be monitored in order to establish an appropriate ERI.

In accordance with an important feature of the present invention, when the ERI is issued by POR/ERI circuit 37, pacemaker 10 switches to "regulation" of all settings other than 5.0- and 7.5-V. With this arrangement, the expected longevity of pacemaker 10 (or, more specifically, of battery 32 in pacemaker 10) is advantageously increased. This arrangement differs from the prior art, in which current-consuming "regulation" circuitry is utilized in the early and middle stages of battery depletion, and disabled near the battery's EOL to maximize remaining useful battery life.

Since the hardware of pacemaker 10 supports "regulation" of all user-programmable amplitude settings, it is contemplated by the inventors that other combinations of "regulated" and "unregulated" operation, pre- and post-ERI, can be advantageously implemented.

For example, it is contemplated that all amplitude settings less than 5.0-V could be implemented as "regulated". This offers the advantage of accuracy in delivered amplitudes less than 5.0-V, but may reduce expected longevity.

Another variation to the disclosed embodiment of the invention is to cause the switch from "unregulated" to "regulated" for certain settings at a time either before or after ERI. It is contemplated that the criteria for deciding to make this switch is not inherently related to ERI criteria, and that some other combination of conditions may be used to trigger the switch to "regulation" of output amplitudes.

From the foregoing detailed description of a preferred embodiment of the invention, it should be apparent that a pacemaker having programmably selectable output amplitudes has been disclosed. The pacemaker includes "regulation" circuitry for controlling the amplitude of delivered pulses. For some settings, the "regulation" circuitry is not utilized until near the end of the battery's life, so that consumption of current by the circuitry is minimized.

Although a specific embodiment of the invention has be described herein in some detail, this has been done for the purposes of illustrating the present invention only, and is not intended to be limiting with respect to the scope of the invention. It is believed that various substitutions, alterations, and modifications, including but not limited to those specifically discussed above, may be made to the disclosed embodiment without departing from the spirit and scope of the present invention as defined in the appended claims, which follow.

What is claimed is:

1. A method of operating a cardiac pacemaker having a battery and an output capacitor for storing a stimulation pulse voltage, said method comprising the steps of:
    (a) monitoring said battery's depletion level;
    (b) when said battery's depletion is below a predetermined level, activating a charging circuit to charge said output capacitor to a voltage proportional to said battery's voltage;
    (c) when said battery's depletion exceeds said predetermined level, activating said charging circuit and a reference voltage comparator circuit to charge said output capacitor to a voltage proportional to a reference voltage.

2. A method according to claim 2 wherein said step of activating said charging circuitry to charge said output capacitor to a voltage proportional to said battery voltage comprises charging a pump capacitor and transferring charge on said pump capacitor to said output capacitor.

3. A method according to claim 2 wherein said step of activating said charging circuitry to charge said output capacitor to a voltage proportional to said reference voltage comprises charging a pump capacitor and transferring charge on said pump capacitor to said output capacitor, measuring voltage on said output capacitor and terminating charging said pump capacitor in response to said voltage on said output capacitor reaching said voltage proportional to said reference voltage.

4. A stimulator having a battery and an output capacitor for storing a stimulation pulse voltage, further comprising:

a charging circuit, coupled to said battery and said output capacitor;

means for monitoring said battery's depletion level;

means responsive to said battery's depletion level being less than a predetermined depletion level for causing said charging circuit to charge said output capacitor to a voltage proportional to said battery's voltage;

means for defining a reference voltage; and means responsive to said battery's depletion exceeding said predetermined depletion level for causing said charging circuit to charge said output capacitor to a voltage proportional to said reference voltage.

5. A stimulator according to claim 4 wherein said charging circuit comprises a pump capacitor, means for charging said pump capacitor and means for transferring charge on said pump capacitor to said output capacitor.

6. A stimulator according to claim 4 wherein said means responsive to said battery's depletion exceeding said predetermined depletion level for causing said charging circuit to charge said output capacitor to a voltage proportional to said reference voltage comprises a comparator coupled to said output capacitor and to said means for defining a reference voltage.

* * * * *